(12) United States Patent
Downie et al.

(10) Patent No.: US 7,434,580 B2
(45) Date of Patent: Oct. 14, 2008

(54) MONITORING MEDICAL GAS XENON CONCENTRATION USING ULTRASONIC GAS ANALYSER

(75) Inventors: Neil Alexander Downie, Guildford (GB); Stuart Alexander Kerr, Knutsford (GB)

(73) Assignee: Air Products and Chemicals, Inc., Allentown, PA (US)

( * ) Notice: Subject to any disclaimer, the term of this patent is extended or adjusted under 35 U.S.C. 154(b) by 486 days.

(21) Appl. No.: 10/512,797

(22) PCT Filed: May 1, 2003

(86) PCT No.: PCT/GB03/01877

§ 371 (c)(1),
(2), (4) Date: Jul. 8, 2005

(87) PCT Pub. No.: WO03/093812

PCT Pub. Date: Nov. 13, 2003

(65) Prior Publication Data

US 2006/0021421 A1 Feb. 2, 2006

(30) Foreign Application Priority Data

May 1, 2002 (GB) .................................. 0210021.2

(51) Int. Cl.
*A62B 7/10* (2006.01)
*A62B 23/02* (2006.01)
*A62B 7/00* (2006.01)
*A61M 16/00* (2006.01)

(52) U.S. Cl. ............................ 128/205.28; 128/205.27; 128/203.25; 128/203.12; 128/204.18; 128/204.22; 128/205.12; 128/200.16; 128/200.11; 128/203.15; 128/200.19

(58) Field of Classification Search ............ 128/200.16, 128/200.11, 203.15, 200.19, 201.21, 203.12, 128/203.25, 205.27, 205.28
See application file for complete search history.

(56) References Cited

U.S. PATENT DOCUMENTS 4,424,703 A  1/1984  Winter et al.
(Continued)

FOREIGN PATENT DOCUMENTS

DE  2945172  10/1979
(Continued)

OTHER PUBLICATIONS

Draeger Medizintechnik GmbH, Instrument determines molarity of xenon in nhaled air with rapid respons—includes piezoeletric transducers establishing measurement path in chamber with sound absorbent cladding; Aug. 6, 1998; Derwnet-Acc-No. 1998-429307.*
(Continued)

*Primary Examiner*—Justine R Yu
*Assistant Examiner*—Clinton Ostrup
(74) *Attorney, Agent, or Firm*—Willard Jones, II

(57) ABSTRACT

The concentration of xenon, in a medical gas mixture of xenon as an active component with a known composition of oxygen and, optionally, nitrogen and/or helium recirculating through a medical device (103) in which carbon dioxide is introduced into the mixture, is monitored by removal (135, 133) of carbon dioxide downstream of the medical device (103) and subsequently passing the carbon dioxide-free gas through an ultrasonic gas analyser (143) upstream of the medical device. The gas analyzer determines the xenon concentration by measuring the time delay between transmission of an ultrahigh frequency ultrasonic pulse of at least 100 kHz axially through the sample chamber from a location at one end thereof and reflection of said pulse axially from the other end of the sample chamber back to said location. An analyser of novel construction is disclosed.

25 Claims, 2 Drawing Sheets

U.S. PATENT DOCUMENTS

Figure 1:
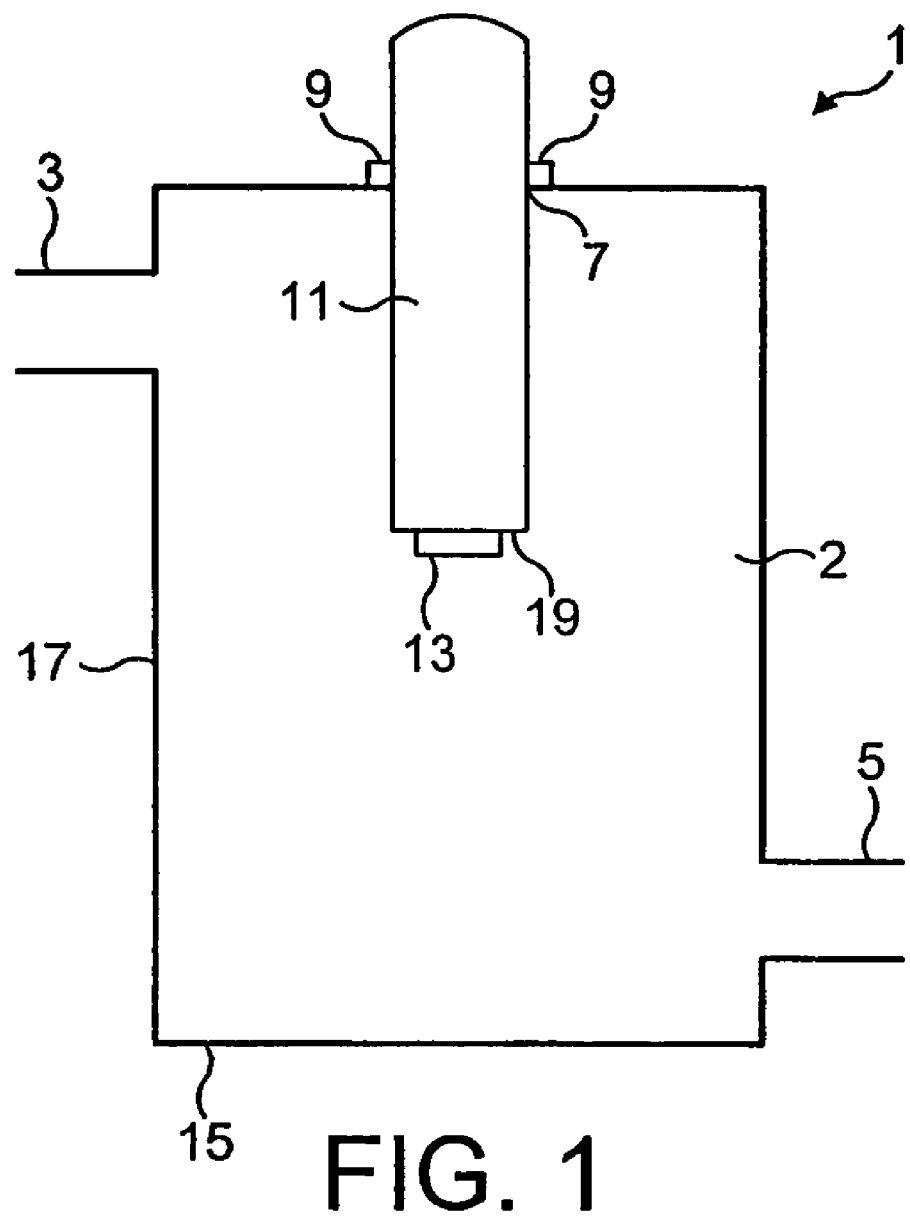

| | | | | |
|---|---|---|---|---|
| 4,622,976 | A | * | 11/1986 | Timpe et al. ................. 600/431 |
| 5,060,514 | A | | 10/1991 | Aylsworth |
| 6,192,739 | B1 | * | 2/2001 | Logue et al. ............... 73/24.01 |
| 6,279,378 | B1 | | 8/2001 | Sheen et al. |
| 6,408,849 | B1 | * | 6/2002 | Spiegelman et al. ... 128/205.27 |
| 6,536,429 | B1 | * | 3/2003 | Pavlov et al. .......... 128/203.26 |
| 6,680,994 | B2 | * | 1/2004 | Jones et al. ................. 376/250 |
| 2005/0235831 | A1 | * | 10/2005 | Taveira et al. ................. 96/111 |

FOREIGN PATENT DOCUMENTS

| | | | |
|---|---|---|---|
| DE | 29807286 U1 | * | 8/1998 |
| WO | WO 00/53192 A1 | * | 9/2000 |
| WO | WO 01/08692 A1 | * | 2/2001 |

OTHER PUBLICATIONS

Search Report issued on Dec. 19, 2002 in respect of UK Patent Application No. 0210021.2.

* cited by examiner

MONITORING MEDICAL GAS XENON CONCENTRATION USING ULTRASONIC GAS ANALYSER

The present invention relates to a method and apparatus using the gas specific property of speed of sound for monitoring the concentration of xenon in a medical gas mixture with oxygen and, optionally, nitrogen recirculating through a medical device introducing carbon dioxide into the mixture.

Apparatus and methods for determining the concentration of components in gas mixtures using sonic or ultrasonic transmission/detection systems are known. The concentration can be determined by phase or pulse measurements (see, for example, U.S. Pat. No. 6,192,739) and it is known to use the time for a pulse to be reflected one or more times across an internally reflective housing having the transmitter and receiver located at the same or different ends of the housing.

For example, U.S. Pat. No. 5,060,514 discloses an ultrasonic gas measuring device which has a cylindrical housing having transmitting and receiving means provided on opposite end walls of the housing. Gas flows axially through the housing from an inlet in the end wall having the transmitter to an outlet in the opposite end wall. At least at some instance during its flow through the housing, the gas flow is divided so as to reduce gas flow turbulence. Electronic circuitry in the device is designed to generate a signal corresponding to the ultrasonic radiation detected having passed through the gas sample, which is compared with a reference signal provided to the transmitting transducer and the resulting phase shift used to compute the concentration of the gas. The device is particularly applicable to the analysis of oxygen concentration in medical devices used by respiratory patients.

In another example, U.S. Pat. No. 6,279,378 discloses an apparatus and method utilizing high frequency ultrasonic waves, especially of about 0.5 MHz, for analysing gases so as to measure trace amounts of gases in an air sample. The sample is drawn through an acoustic chamber using a low speed air pump and the sound velocity and acoustic attenuation of sound waves travelling through the gas/air mixture compared with that of air alone. The acoustic chamber of the device is small, the exemplified distance between a pair of transmitters/receivers typically being 0.64 cm but the wave is reflected back and forth across the chamber several times, for example five reflections. The speed of sound and the time of flight (TOF) over 11.43 cm is listed for several gases, including xenon, together with the difference in TOF as compared with air alone.

Xenon has long been known as an anaesthetic gas used in admixture with oxygen and optionally also helium, but has not been extensively used as such. More recently, there has been interest in other medical uses for xenon. In particular, WO-A-0053192 discloses the use of xenon to treat neurointoxications such as caused by apoplexy, drug abuse, oxygen deficiency during birth, Parkinson's disease, schizophrenia, Giulles de la Tourette syndrome, craniocerebral trauma or migraine and refers to the use of xenon in a cardio-pulmonary bypass machine. Further, WO-A-0108692 discloses the use of xenon as an NMDA antagonist to, for example, provide neuroprotection, relieve neuropathic pain or inhibit synaptic plasticity.

Xenon has limited availability in that it is usually extracted from air, in which it constitutes only 0.000039 percent by weight (0.0000087 percent by volume). Accordingly, it is desirable to recover or reuse xenon in any application and the need for such recovery or reuse will increase with increasing demand for xenon. In particular, it is desirable to recirculate xenon through medical devices. However, it is necessary to carefully monitor, and adjust, the xenon concentration in a recirculating medical gas and hence the need exists for a simple and relatively inexpensive means for providing a rapid and reasonably accurate monitoring of xenon concentration in recirculating medical gas. Although ultrasonic methods have been proposed to measure xenon concentration as a contaminant, the active concentration of xenon in medical gases is substantially higher than contaminant level and the presence of carbon dioxide introduced by the medical device would interfere with xenon concentration measurements using ultrasonic measurements.

According to a first aspect of the invention there is provided a method of monitoring the concentration of xenon in a medical gas mixture of xenon as an active component, with a known composition of oxygen and, optionally, nitrogen and/or helium recirculating through a medical device in which carbon dioxide is introduced into the mixture, said method comprising removing carbon dioxide downstream of the medical device and subsequently upstream of the medical device measuring the time delay between transmission of an ultrahigh ultrasonic pulse of at least about 100 kHz axially through the carbon dioxide-free gas mixture in an internally reflective cylindrical sample chamber from a location at one end thereof and reflection of said pulse axially from the other end of the chamber back to said location.

In a second aspect, the present invention provides an apparatus for recirculating a medical gas mixture of xenon with a known composition of oxygen and, optionally, nitrogen and/or helium through a medical device in which carbon dioxide is introduced into the mixture, said apparatus comprising:

a circuit for recirculatory flow of the medical gas mixture to and from said medical device;

a carbon dioxide absorber downstream from the medical device for removing carbon dioxide from the carbon dioxide-contaminated medical gas;

an analyser upstream of the medical device for monitoring the concentration of xenon in the carbon dioxide-free medical gas mixture recirculating within the circuit; said analyser comprising:

an internally reflective cylindrical sample chamber having a gas inlet, an ultrahigh frequency ultrasonic transmitter located at one end of the sample chamber for emitting ultrasonic pulses of at least about 100 kHz axially through the sample chamber, a receiver located at said end of the sample chamber for receiving ultrasonic radiation reflected axially from the other end of the sample chamber, and processing means for determining the time delay between transmission and receipt of an ultrasonic pulse by said transmitter and receiver respectively and correlating said delay with reference data to indicate the concentration of xenon in the medical gas mixture in the sample chamber, and gas replenishment means for introducing make-up gas components to the medical gas mixture to control the composition thereof.

Usually, the gas replenishment means will comprises separate respective inlets into the recirculatory circuit for oxygen and for a xenon/oxygen mixture and, optionally, a separate inlet into the recirculatory circuit for air.

Volumetric means may be provided for monitoring the volume of the carbon dioxide-free medical gas mixture in the recirculatory circuit and/or an analyser for monitoring oxygen concentration in the carbon dioxide-free medical gas mixture in the recirculatory circuit. When the recirculating gas comprises nitrogen and/or helium additional mean usually will be provided for monitoring their concentration.

In a third aspect of the invention, there is provided an analyser for use in the method of the invention, said analyser comprising:

an internally reflective cylindrical sample chamber having a gas inlet and a gas outlet located at axially and peripherally spaced locations in the side walls thereof with the gas inlet behind the transmitting surface of the transmitter whereby flow of gas through the chamber has an axial component;

an ultrahigh frequency ultrasonic transmitter located at one end of the sample chamber for emitting ultrasonic pulses of at least about 100 kHz axially through the sample chamber;

a receiver located at said end of the sample chamber for receiving ultrasonic radiation reflected axially from the other end of the sample chamber; and processing means for determining the time delay between transmission and receipt of an ultrasonic pulse by said transmitter and receiver respectively and correlating said delay with reference data to indicate the concentration of the xenon in a gas mixture in the sample chamber.

The analyser preferably operates at a pressure of up to about 250 millibar gauge (mbarg) (125 kPa), more preferably up to about 150 mbarg (115 kPa) and the apparatus may provide gas to the medical device at a pressure of up to about 100 mbarg (110 kPa), but preferably about 30 mbarg (103 kPa).

The transmitter and receiver may be separate but preferably a single combined transmitter/receiver is used.

The frequency of the ultrahigh ultrasonic radiation used in the method is greater than about 100 kHz and more preferably greater than about 250 kHz. Preferably, the frequency is less than about 400 kHz and still more preferably about 380 kHz. The use of ultrahigh ultrasonic radiation allows a very narrow beam of pulses to be transmitted, which minimizes multiple reflections and thus improves the accuracy of the measurement. It also enables the sample chamber to be minimized in size whilst maintaining the desired level of accuracy in the measurement.

Preferably the sample chamber is made from a polished low thermal expansion material and is preferably of circular cross section. It also is preferred to have a volume of less than about 500 cm$^3$ and more preferably less than about 200 cm$^3$ Preferably, the measurement of the content of gas is of an accuracy of less than about ±5%, more preferably less than about ±2%, still more preferably less than about ±1% and most preferably less than about ±0.5%.

The accuracy of measurement is dependent on inter alia the path length of the pulse, the overall volume of the sample chamber and the frequency of the ultrahigh ultrasonic radiation. However, if minimizing the size of the sample chamber is important in the use of the analyser, such as to provide rapid information regarding changes in the composition of a circulating medical gas mixture, the level of accuracy may be compromised to enable rapid analysis of the composition.

Preferably, in order to reduce the risk of affecting the measurement by refractive deflection of the beam, as may occur if a jet of gas from the gas inlet is introduced directly toward the transmitting surface of the transmitter, the gas inlet to the sample chamber is behind the transmitting surface. More preferably, the gas inlet and gas outlet to the sample chamber are located at axially and peripherally spaced locations in the side walls of thereof whereby flow of gas though the chamber has an axial component.

The accuracy of the measurement provided by the method and apparatus of the invention is only slightly affected by small variations in temperature and readily can be approximately corrected by a correction signal derived from a temperature sensitive electronic component. Similarly, provided that a reasonable gas flow pattern is achieved, it is believed that the measurement is not significantly affected by variations in flow rate. However, in order to maximize the accuracy in the measurement, the device may be calibrated before use by passing pure xenon through the sample chamber at approximately the flow rate to be used.

The method and apparatus of the present invention is particularly applicable to the measurement of gas mixtures used in cardiopulmonary bypass oxygenators or artificial ventilators.

When, as often in the case of spent medical gases, the gas mixture contains, in addition to carbon dioxide, water vapour and/or other components which absorb energy at high ultrasonic frequencies, it is usually necessary to remove, or at least reduce, the content of said components prior to analysis to prevent interference with the analysis.

Figure 2:
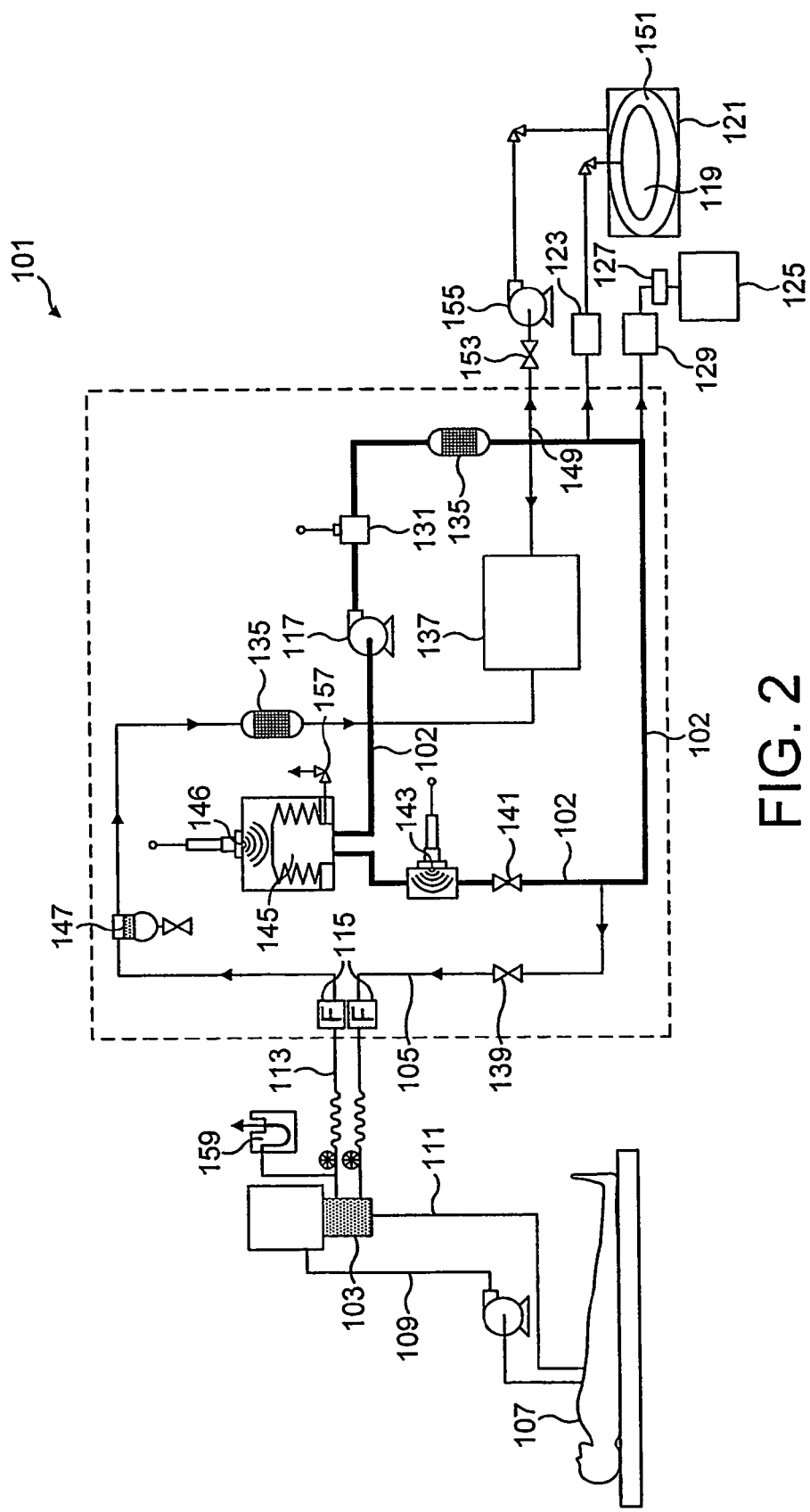

The following is a description by way of example only and with reference to the accompanying drawings of presently preferred embodiments of the invention. In the drawings:

FIG. 1 is a cross-sectional side view of an analyser in accordance with the present invention and FIG. 2 is a diagrammatic representation of the use of the analyser of FIG. 1 in a gas recirculation system for providing gas to a cardiopulmonary bypass oxygenator.

With reference to FIG. 1, the gas analyser (generally designated 1) for determining the composition of a gas mixture comprises a hollow internally smooth stainless steel cylinder 17, which defines a sample space 2 for the sample of gas to be analysed, and has a gas inlet 3 and a gas outlet 5 and an aperture 7. An ultrahigh frequency ultrasonic gauge 11 is held in aperture 7 by ring seal 9 and the opposing wall 15 of the cylinder 17 reflects ultrasonic pulses emitted by the gauge. The gauge 11 comprises a transducer 13, for emitting ultrasonic radiation, on the lowermost surface 19 of gauge 11. The transducer also acts as an ultrasonic receiver and is connected to a microprocessor (not shown) for linearizing the data generated by the analyser.

In use, the analyser is used to measure the proportion of a gas in a mixture, preferably oxygen and xenon, by emitting ultrasonic radiation at 380 KHz from transducer 13 through the sample chamber 2, which contains the gas mixture passing through the device via gas inlet 3 and gas outlet 5, and receiving the radiation reflected from opposing wall, with receiver 19. The data is transferred to the microprocessor where it is manipulated to show the relative proportions of gases in the mixture.

With reference to FIG. 2, a xenon/oxygen mixture in a ratio of 80% xenon to 20% oxygen is fed into the main circuit 102 of the apparatus (generally designated 101) from a xenon/oxygen supply in fresh gas space 119 of container 121 via xenon mass flow controller (MFC) 123.

The oxygen content of main circuit 102 is topped up from oxygen cylinder 125 via regulator 127 and oxygen mass flow controller (MFC) 129.

One or more (preferably four) diaphragm pumps 117 pump the xenon/oxygen mixture around the circuit 102 at a rate of up to 20 liters per minute (1/min) at a pressure of up to 150 millibar gauge (115 kPa).

The gaseous composition is fed to cardiopulmonary bypass (CPB) oxygenator 103 via medical device supply conduit 105, which is regulated by flow control valve 139, which may be set at a desired level by the operator.

CPB oxygenator 103, which is typically a membrane oxygenator, is fed unoxygenated blood from a patient 107 via unoxygenated blood conduit 109 and returned to the patient 107 via oxygenated blood conduit 111. Spent gas from the CPB oxygenator 103 is fed through spent gas return conduit 113 and then through water trap 147 and primary carbon dioxide absorber 135 to return to the main circuit 102 upstream of pump(s) 117.

Gas passing through the spent gas return conduit 113 and medical device supply conduit 105 pass through respective bacterial filters 115 to protect the patent 107 from contamination from the apparatus 101 and vice versa.

In order to ensure that a constant flow of gas at the set pressure is supplied to the oxygenator 103 and thus available to the patient's blood, gas circulates through the main circuit 102 via pressure maintaining valve 141 downstream from the outlet to medical device supply conduit 105. Pressure maintaining valve 141 is a valve which allows gas flow only when the pressure exceeds a predetermined level, for example 30 mbarg (103 kPa) and accordingly maintains a constant pressure between the pumps 17 and the valve 141.

Downstream from the pressure maintaining valve 141, the gaseous composition is analysed for xenon content using the ultrasonic xenon analyser 143 of FIG. 1. In an alternative arrangement (not shown) the xenon analyser is located upstream of the pressure maintaining valve 141.

The gas is then fed via bellows 145, which expand to take up any additional volume of gas in the apparatus or contract to compensate for loss of volume in the apparatus, and receives the spent gas upstream of pump(s) 117.

The oxygen concentration in the main circuit 102 is monitored by oxygen fuel cell sensor 131 that is shown situated in the main circuit 102 downstream from pump(s) 117 but could be located downstream of the pressure maintenance valve 141. The gas is then fed through backup carbon dioxide absorber 133, which removes residual carbon dioxide from the recirculating gas. The carbon dioxide removed by absorbers 133 and 135 has entered via the oxygenator 103 after being flushed from the patient's blood. At least absorber 135 should be replaced with each use of the system.

Downstream from the backup carbon dioxide absorber 133, a small sample of gas is drawn from the main circuit 102 and fed to analyser unit 137 to be analysed for carbon dioxide, via an infra red gas analyser, to ensure that the carbon dioxide absorbers are working efficiently and for oxygen, via a paramagnetic gas analyser, as a backup to the oxygen fuel cell sensor 131. The sample is returned to the main circuit 102 upstream from the pump(s) 117.

Recovery gas conduit 149 selectively feeds at least a portion of gas from the main circuit 102 at a point downstream from the backup carbon dioxide absorber 133 to the ullage space 151 of container 121, via recovery valve 153 and compressor 155. This container 121 is of the kind described in our co-pending UK Patent Application No. 0210022.0 filed 1$^{st}$ May 2002 and the corresponding PCT Patent Application of even date with the present application (file reference P8943WO).

An atmospheric vent 157 from bellows 145 enables the gas within the apparatus to be vented to atmosphere if desired.

There is a U-tube relief device 159 on the spent gas return conduit 113 to protect the oxygenator 103 and patient 107 in the event of any back pressure from the apparatus 101.

Addition of fresh gas to the apparatus is controlled by an analog electronic circuit (not shown) between oxygen fuel cell sensor 131 and oxygen MFC 129 for fresh oxygen addition and by an analog electronic circuit between an ultrasonic level sensor 146 measuring the position of the bellows and the xenon MFC 123 for fresh xenon/oxygen mixture addition.

As well as monitoring the concentration of oxygen in the main circuit 102, oxygen fuel cell sensor 131 enables the oxygen concentration to be controlled. The operator may choose a set point on the sensor 131 corresponding to the desired oxygen concentration. When oxygen concentration measured by sensor 131 falls below the set point, oxygen MFC 129 is triggered to feed fresh oxygen into the main circuit 102 at a rate proportional to the difference between the oxygen level set point and the oxygen sensor 131 measurement via a high gain circuit connecting oxygen MFC 129 to sensor 131.

Typically, the high gain oxygen control circuit (not shown) will have a gain of 1, corresponding to an oxygen flow rate through oxygen MFC 129 and into the main circuit 102 of 1 l/min for every 1% difference between the oxygen set point and the measured oxygen level.

The xenon concentration of the main circuit is controlled by ultrasonic bellows level sensor 146. The operator may set the desired level on a potentiometer (not shown) connected to sensor 146, which corresponds to an expanded level of the bellows 145. This level corresponds to the volume in the system and, given that the oxygen concentration is known, to a desired concentration of xenon. When the sensor 146 detects that the bellows 145 has fallen below the desired level, xenon MFC 123 is triggered to feed fresh oxygen/xenon mixture into the main circuit 102 at a rate proportional to the difference between the potentiometer set point and the level measured by bellows sensor 146, via a low gain circuit (not shown) connecting sensor 146 to xenon MFC 123.

Typically, the xenon low gain circuit will have a gain of 0.1, corresponding to a flow of fresh xenon/oxygen mixture into the main circuit 102 of 0.1 l/min for every 1% difference between the potentiometer setpoint and the level measured by bellows sensor 146.

The various sensor readings and flow rates are displayed on a monitoring unit (not shown).

In use, oxygen is consumed and replaced by carbon dioxide via the CPB oxygenator 103. The operator may select the flow rate to the oxygenator 103 by using flow control valve 139. This effectively controls the rate that carbon dioxide is flushed from patient's blood into the apparatus and hence provides some control as to the relative acidity or alkalinity of the patient 107.

Carbon dioxide is absorbed by primary carbon dioxide absorber 135 and the reduction in the oxygen level is detected by fuel cell sensor 131 triggering, via the high gain circuit, replenishment of oxygen levels under the control of oxygen MFC 129.

Xenon sensor 143 measures the xenon concentration in the main circuit 102. This reading may be compared to other readings to reach various conclusions. For example, if the oxygen concentration measured by oxygen fuel cell sensor 131 does not equal 100 minus the xenon concentration measured by xenon sensor 143, it is indicative of contamination, for example by carbon dioxide or nitrogen, and the operator may be alerted to vent the apparatus to atmosphere or recover the used gas. Alternatively, this may be done automatically at a preset level. The xenon sensor 143 is also used to monitor the xenon concentration predicted from the level of the bellows. Similarly, if these two readings do not agree, this may be indicative of too much carbon dioxide, nitrogen or oxygen. As a result, the operator may again choose to vent to atmosphere or recover the used gas.

If the gas volume in the apparatus is increased, the level of bellows 145 increases. If the level of bellows 145 exceeds a preset level, gas is vented from the apparatus, again either manually or automatically, via atmospheric vent 157 and/or xenon recovery valve 153. Optionally, the sensor 146 may be connected to ultrasonic analyser 143 so that when the bellows 145 upper level is exceeded, vent 157 or valve 153 is selectively opened depending on the xenon content of the gas measured by analyser 143.

Although illustrated and described herein with reference to certain specific embodiments, the present invention is nevertheless not intended to be limited to the details shown. Rather, various modifications may be made in the details within the spirit and scope of the following claims.

The invention claimed is:

1. A method of monitoring concentration of xenon in a medical gas mixture recirculating through a medical device in which carbon dioxide is introduced into the mixture resulting in a carbon dioxide-contaminated gas mixture, said medical gas having xenon as an active component and being selected from oxygen-containing mixtures consisting of oxygen and xenon and mixtures of xenon with a composition consisting of oxygen and nitrogen and/or helium in known proportions, said method comprising removing carbon dioxide from said carbon dioxide-contaminated gas mixture downstream of the medical device to provide a carbon dioxide-free gas mixture and subsequently upstream of the medical device the concentration of xenon is measured by measuring a time delay between transmission of an ultrahigh ultrasonic pulse of at least 100 kHz axially through the carbon dioxide-free gas mixture in an internally reflective cylindrical sample chamber from a location at one end thereof and reflection of said pulse axially from the other end of the chamber back to said location.

2. The method according to claim 1, wherein the medical gas mixture is a binary gas mixture of xenon and oxygen.

3. The method according to claim 1, wherein the medical gas mixture is a tertiary gas mixture of xenon, oxygen and nitrogen.

4. The method according to claim 1, wherein the medical device is a cardiopulmonary bypass oxygenator.

5. The method according to claim 1, wherein the medical device is an artificial ventilator.

6. The method according to claim 1, wherein the ultrasonic pulse has a frequency of greater than 250 kHz.

7. The method according to claim 1, wherein the ultrasonic pulse has a frequency of less than 450 kHz.

8. The method according to claim 1, wherein the ultrasonic pulse has a frequency of about 380 kHz.

9. An analyser for use in the method of claim 1, said analyser comprising:
an internally reflective cylindrical sample chamber having a gas inlet and a gas outlet located at axially and peripherally spaced locations in the side walls thereof with the gas inlet behind the transmitting surface of the transmitter whereby flow of gas through the chamber has an axial component;
an ultrahigh frequency ultrasonic transmitter located at one end of the sample chamber for emitting ultrasonic pulses of at least 100 kHz axially through the sample chamber;
a receiver located at said end of the sample chamber for receiving ultrasonic radiation reflected axially from the other end of the sample chamber; and
processing means for determining the time delay between transmission and receipt of an ultrasonic pulse by said transmitter and receiver respectively and correlating said delay with reference data to indicate the concentration of xenon in a gas mixture in the sample chamber.

10. The analyser according to claim 9, wherein the sample chamber has a volume of less than 200 cm$^3$.

11. The analyser according to claim 9, wherein the transmitter emits ultrasonic radiation at a frequency of less than 400 kHz.

12. The analyser according to claim 9, wherein the transmitter emits ultrasonic radiation at a frequency of greater than 250 kHz.

13. The analyser according to claim 12, wherein the transmitter emits ultrasonic radiation at a frequency of about 380 kHz.

14. An apparatus for recirculating a medical gas mixture, selected from oxygen-containing mixtures consisting of oxygen and xenon and mixtures of xenon with a composition consisting of oxygen and nitrogen and/or helium in known porportions, through a medical device in which carbon dioxide is introduced into the mixture resulting in a carbon dioxide-contaminated medical gas mixture, said apparatus comprising:
a circuit for recirculatory flow of the medical gas mixture to and from said medical device;
a carbon dioxide absorber downstream from the medical device for removing carbon dioxide from the carbon dioxide-contaminated medical gas mixture to provide a carbon dioxide-free gas mixture;
an analyser upstream of the medical device for monitoring a concentration of xenon in the carbon dioxide-free medical gas mixture recirculating within the circuit; said analyser comprising:
an internally reflective cylindrical sample chamber having a gas inlet,
an ultrahigh frequency ultrasonic transmitter located at one end of the sample chamber for emitting ultrasonic pulses of at least 100 kHz axially through the sample chamber,
a receiver located at said end of the sample chamber for receiving ultrasonic radiation reflected axially from the other end of the sample chamber, and
processing means for determining the time delay between transmission and receipt of an ultrasonic pulse by said transmitter and receiver respectively and correlating said delay with reference data to indicate the concentration of xenon in the medical gas mixture in the sample chamber, and
gas replenishment means for introducing make-up gas components to the medical gas mixture to control the constitution thereof.

15. The apparatus according to claim 14, wherein the gas inlet and gas outlet to the analyser sample chamber are located at axially and peripherally spaced locations in the side walls thereof and the gas inlet is behind the transmitting surface of the transmitter, whereby flow of gas through the chamber has an axial component.

16. The apparatus according to claim 14, wherein the sample chamber has a volume of less than 200 cm$^3$.

17. The analyser according to claim 14, wherein the transmitter emits ultrasonic radiation at a frequency of less than 400 kHz.

18. The apparatus according to claim 14, wherein the transmitter emits ultrasonic radiation at a frequency of greater than 250 kHz.

19. The apparatus according to claim 18, wherein the transmitter emits ultrasonic radiation at a frequency of about 380 kHz.

20. The apparatus according to claim 14, wherein the gas replenishment means comprises separate respective inlets into the recirculatory circuit for oxygen and for a xenon/oxygen mixture.

21. The apparatus according to claim 20, wherein the gas replenishment means further comprises a separate inlet into the recirculatory circuit for air.

22. The apparatus according to claim 14, further comprising volumetric means for monitoring the volume of the carbon dioxide-free medical gas mixture in the recirculatory circuit.

23. The apparatus according to claim 14, further comprising an analyser for monitoring oxygen concentration in the carbon dioxide-free medical gas mixture in the recirculatory circuit.

24. A method of monitoring concentration of xenon in a medical gas mixture recirculating through a medical device in which carbon dioxide is introduced into the mixture resulting in a carbon dioxide-contaminated gas mixture, said medical gas having xenon as an active component and being selected from oxygen-containing mixtures consisting of oxygen and xenon and mixtures of xenon with a composition consisting of oxygen and nitrogen and/or helium in known proportions, said method comprising removing carbon dioxide from said carbon dioxide-contaminated gas mixture downstream of the medical device to provide a carbon dioxide-free gas mixture; measuring a time delay between transmission of an ultrahigh ultrasonic pulse of at least 100 kHz axially through the carbon dioxide-free gas mixture in an internally reflective cylindrical sample chamber from a location at one end thereof and reflection of said pulse axially from the other end of the chamber back to said location; and correlating said delay with reference data to generate a signal proportionate to the concentration of xenon in said carbon dioxide-free gas mixture.

25. A method of maintaining concentration of xenon in a medical gas mixture recirculating through a medical device in which carbon dioxide is introduced into the mixture resulting in a carbon dioxide-contaminated gas mixture, said medical gas having xenon as an active component and being selected from oxygen-containing mixtures consisting of oxygen and xenon and mixtures of xenon with a composition consisting of oxygen and nitrogen and/or helium in known proportions, said method comprising removing carbon dioxide from said carbon dioxide-contaminated gas mixture downstream of the medical device to provide a carbon dioxide-free gas mixture; measuring a time delay between transmission of an ultrahigh ultrasonic pulse of at least 100 kHz axially through the carbon dioxide-free gas mixture in an internally reflective cylindrical sample chamber from a location at one end thereof and reflection of said pulse axially from the other end of the chamber back to said location; correlating said delay with reference data to generate a signal proportionate to the concentration of xenon in said carbon dioxide-free gas mixture; and introducing make-up xenon to the medical gas mixture to maintain the concentration thereof.

* * * * *